United States Patent [19]

Honda

[11] Patent Number: 5,610,811
[45] Date of Patent: Mar. 11, 1997

[54] SURGICAL INSTRUMENT FILE SYSTEM

[75] Inventor: Hiroshi Honda, Funabashi, Japan

[73] Assignee: Niti-on Medical Supply Co., Ltd., Chiba-ken, Japan

[21] Appl. No.: 445,487

[22] Filed: May 22, 1995

Related U.S. Application Data

[63] Continuation-in-part of Ser. No. 146,367, Oct. 28, 1993, abandoned.

[30] Foreign Application Priority Data

Nov. 9, 1992 [JP] Japan ................................ 4-322232

[51] Int. Cl.⁶ .......................... G06F 17/60; G09B 23/28
[52] U.S. Cl. ...................... 395/202; 235/375; 235/385; 434/262; 395/228
[58] Field of Search ................................. 364/401, 403, 364/478, 479; 40/913; 235/375, 385, 454, 462, 487, 488, 495; 433/77, 79, 141, 229; 434/219, 262, 365, 367; 206/570

[56] References Cited

U.S. PATENT DOCUMENTS

| | | | |
|---|---|---|---|
| 4,276,112 | 6/1981 | French et al. | 156/360 |
| 4,631,465 | 12/1986 | Fukuyama et al. | 318/565 |
| 4,671,916 | 6/1987 | Hamas | 264/249 |
| 4,900,252 | 2/1990 | Liefke et al. | 433/27 |
| 4,922,591 | 5/1990 | Campbell | 483/1 |
| 4,939,354 | 7/1990 | Priddy et al. | |
| 4,943,939 | 7/1990 | Hoover | 364/555 |
| 5,046,014 | 9/1991 | Anjo | 364/474.02 |
| 5,334,822 | 8/1994 | Sanford | 235/385 |
| 5,443,082 | 8/1995 | Mewburn | 128/897 |
| 5,449,892 | 9/1995 | Yamada | 235/462 |

FOREIGN PATENT DOCUMENTS

| | | | |
|---|---|---|---|
| WO91/15159 | 10/1991 | WIPO | A61B 19/02 |
| WO93/09514 | 5/1993 | WIPO | G06K 7/10 |

OTHER PUBLICATIONS

Dialog Abstract: File 256, Acc# 01014731; LEGI 4.4.0; Weber Marking Systems, Inc.; Date of Release: Apr. 1978.
Dialog Abstract: File 15, Acc# 00226809; "Source Marking Slashes Errors, Speeds Throughput/'Why We Add Drawings to Our Carton Labels'"; *Modern Materials Handling;* v39 n1; pp. 62–65; Jan. 9, 1984.
Dialog Abstract: File 15, Acc# 00382688; Fodor; "Encode, Label and Scan Your Way to Productivity"; *Industrial Distribution;* v76 n11; pp. 61–67; Nov. 1987.
Dialog Abstract: File 16, Acc# 02045312; "New Process for Application of Bar Codes Directly on Metal is Announced"; Solution Technology; News Release; Aug. 8, 1988; p. 1.
Dialog Abstract: File 155, Acc# 08005580; Cowlard; "Annotated Tray Lists Save Time, Decrease Errors"; *Supply, Processing, and Distribution Department, Thomas Jefferson University Hospital, Philadelphia;* Jan. 1992, 5(1); pp. 286–288, 290–292.
Friedman et al.; "Dentist's Checklist & Tray Setup System"; On the Mark Computer Software Co.; released Oct. 1988; Dialog: File 278, ACC# 0013366.

*Primary Examiner*—Gail O. Hayes
*Assistant Examiner*—Stephen R. Tkacs
*Attorney, Agent, or Firm*—Frank J. Jordan

[57] ABSTRACT

A surgical instrument file system comprised of a screen on which the names and pictures of surgical instruments required for a surgical procedure are selectively displayed; surgical instruments to which a unique optically readable code mark such as a bar code is attached; a reader for reading the optically readable code mark; and a computer which stores the data about surgical instruments for the surgical procedure and into which the information from the optically readable code mark is inputted. The optically readable code mark on a surgical instrument is read by the reader and inputted into the computer, by which the read and inputted surgical instruments are successively identified on a screen, and finally the preparation of surgical instrument sets can be confirmed.

25 Claims, 15 Drawing Sheets

| DEPARTMENT SELECTION | | OPERATION TYPE |
|---|---|---|
| ● INTERNAL MEDICINE | ◎ UROLOGY | ☒ GASTRODUODENUM |
| ◎ NO. 2 SURGERY | ◎ COMMONNESS | ☐ ABDOMINAL HERNIA |
| ◎ ORAL SURGERY | | ☐ CYSTIC |
| ◎ DERMATOLOGY | | ☐ LIVER |
| ◎ OPTHALMOLOGY | | ☐ - - - - |
| ◎ OTORHINOLARYNGOLOGY | | |
| ◎ ORTHOPEDIA | NEXT | OK |
| ◎ OBSTETRICS AND GYNECOLOGY | PHOTO ☒ | HELP |
| ◎ CEREBRAL SURGERY | LIST ☐ | END |

FIG. 4

NAME: ABC

PHOTO-1

PHOTO-2

PHOTO-3

TYPE:
CLASS:
MANUFACTURE DATE:
MAKER:
CATALOGUE NO.:
SIZE:
UNIT:
INSURANCE: ◎ X
INFORMATION

SURGICAL INSTRUMENT FILE SYSTEM

This application is a continuation-in-part of application Ser. No. 08/146,367, filed Oct. 28, 1993, now abandoned.

BACKGROUND OF THE INVENTION

1. Field of the Invention

The present invention relates to a surgical instrument file system which can simply and exactly prepare or assemble surgical instrument sets used for various operations performed in hospitals in response to the surgical procedure (type of operation) performed. More particularly, it relates to a surgical instrument file system in which an optically readable code mark such as a bar code is attached to the surgical instrument. A surgical instrument list for the surgical procedure is stored in a computer. The bar code or other symbol is read with a reader and inputted into the computer, by which surgical instrument is compared with the surgical instrument list stored in the computer.

2. Description of the Related Art

A huge number of surgical instruments are used in hospitals. Particularly in recent times, advances in medical technology have made highly sophisticated surgical operations possible. As a result, the type and number of surgical instruments used for surgical operations has increased greatly as compared with conventional ones. The management and preparation of such a huge number of these surgical instruments requires much labor.

Hitherto, the surgical instruments have generally been handled as shown in FIG. 1: They are cleaned after operation, sorted, and then stored in an instrument cabinet. After that, the instruments are assembled in accordance with the type of surgical operation, and subjected to sterilization processing. Before being used for operation, the instruments are unpacked.

Since many types and sizes of surgical instruments are used for an operation, the work from sorting to assembly in accordance with the surgical procedure requires expert knowledge. Therefore, this work is usually done by skilled nurses.

If such work is done by skilled nurses, however, a shortage of nurses results which omits the time spent for nursing and operating room assisting, the intrinsic jobs of nurses.

Further, due to the recent advances in medical technology the number of types of surgical instruments and the total number of instruments have increased. In addition there are many instruments of similar shape. Therefore, it is difficult for even skilled nurses to assemble surgical instrument sets in accordance with the surgical procedure.

Moreover, a surgical instrument usually has several familiar names in addition to its formal name. Therefore, it is difficult to correctly assemble surgical instrument sets only by name. If the surgical instruments can be assembled and prepared by a person who has no such expert knowledge as nurses have, nurses can do their intrinsic jobs, which serves to the shortage of nurses.

Because recent advances in medical technology have resulted in increases in the total number of surgical instruments, if it can be confirmed that a complete set of surgical instruments has been prepared for the surgical procedure, the safety of the surgical operation can be enhanced.

Further, if the shape of the surgical instrument as well as its name can be confirmed by means of a picture, the instruments required for the operation can be prepared correctly, even if the formal name or the shape of the surgical instrument is not exactly known.

If a surgical instrument is not selected by its name, but inversely the name of instrument is discovered from its shape, it is possible to prepare surgical instrument sets even if the name of the instrument is unknown. Also, the name of the surgical instrument can be found so that even a novice can learn the names of surgical instruments in a short time.

SUMMARY OF THE INVENTION

In view of the above-described problems of the known art, the present invention is aimed at providing a surgical instrument file system which is used for the sorting and assembly of surgical instruments by means of a computer.

To this end, according to the present invention, there is provided a surgical instrument file system comprised of a screen on which the names and pictures of the surgical instruments required for the surgical procedure are selectively displayed; surgical instruments to which a unique optically readable code mark is attached; a reader for reading the optically readable code mark; and a computer which stores data about the surgical instruments required for the surgical procedure and into which the information from the optically readable code mark is inputted. The reader reads the optically readable code mark on the surgical instrument and the information contained in the optically readable code mark is inputted into the computer, after which the computer screen can be checked to confirm what instruments have been read and inputted.

Further, by reading the optically readable code mark with the reader and by inputting the information into the computer, the surgical instruments which have been read and inputted are successively identified on the screen, and completion of the preparation of surgical instruments can be confirmed.

To provide against the case where the reading of the optically readable code marks becomes impossible due to damage to the code during use, a unique visually readable code mark is attached to the surgical instrument in addition to the unique optically readable code mark.

Next, the operation of the present invention will be described below.

The list of surgical instruments for the surgical procedure has been stored by their names and-shapes in the computer. When it is difficult to recognize the shape of an individual surgical instrument in a set figure, a photograph or a partially expanded photograph of the individual surgical instrument can be displayed on the screen.

A unique optically readable code mark is attached to the surgical instrument. As this optically readable code mark, a binary symbol data code (for example, refer to U.S. Pat. No. 4,939,534) and the like as well as the conventionally used bar code can be used.

With this configuration, a picture of a set of instruments in accordance with a surgical procedure is displayed on the screen, and the surgical instruments are inputted into the computer by means of the reader. Then, the inputted surgical instruments are identified on the screen, and finally the completion of preparation of surgical instruments is confirmed on the screen.

The list of surgical instruments can include linens, disposable supplies, medicines, and large-size machines. They can be incorporated as surgical instruments by the hospital when the system is adopted so as to be displayed as necessary surgical instruments on the screen. For articles such as needles which are too small to directly carry the optically readable code mark or large-size machines which cannot be easily handled photographs are prepared of such articles and/or machines, and the optically readable code mark corresponding to each photograph so that this code mark on the photograph can be read by the reader.

In some cases, as indicated above, the article may be too small to directly carry the optically readable code mark such that the code mark is placed directly on a photograph or other pictorial representation of the instrument. In other situations even when the article is large enough to carry a code mark, the code mark may be placed directly on the article and also directly on a photograph or other pictorial representation of the article. Thus the surgical article assembler or operator can selectively present the article itself or the photograph of the article to the reader to read the code mark on the article itself or the code mark on the photograph of the article. There may be various circumstances where this may be used, for example, where the code mark on the instrument has worn out, the operator can present the photograph thereof to the reader, the photograph confirming to the operator that the correct instrument is being selected by comparing the photograph of the instrument with the actual instrument itself on which the code mark has worn or has otherwise become unusable.

In other cases, the code mark may be placed on a large-size machine and also on a photograph or other pictorial representation of such machine. Thus it might be possible in some situations to present the code mark on the machine for reading by the reader but there may be other circumstances where it may not be practical to do this. In such a case, the operator can present the code mark in the photograph of the machine to the reader. There may be some situations, for example, where a new instrument is being used, that the bar code has not yet been applied to the instrument. In such a case, the bar code can be applied to a photograph or other pictorial representation of the instrument and the bar code on the photograph can be read by the reader as the operator checks the photograph against the instrument itself.

As may be desired, instead of applying the bar code to the instruments themselves, the bar codes can be applied to photographs or other pictorial representations of the instruments so that the instruments for an entire procedure or substantially an entire procedure can be assembled by reading the bar codes on the photographs with the operator being able to compare and check each instrument with the photograph to confirm that the correct instrument is being assembled for the procedure. In such a case, it would not be necessary to place the bar codes on the instruments but rather only on the photographs or other pictorial representation of the instruments.

The term pictorial representation as used herein includes photographs, drawings, diagrams and illustrations which show the surgical article.

Although optically readable code marks other than the bar code may be used, it is preferable to use the above-mentioned code of U.S. Pat. No. 4,939,534 for small steel articles because they have a small area to which to attach the code mark and they are sometimes not flat. When the code of U.S. Pat. No. 4,939,534 is used, it is preferable to engrave the code mark by laser beam machining in order to enhance the durability of the code mark. Needless to say, other types of code marks may be used.

These and other objects, features and advantages of the invention will become more apparent from the following description of the preferred embodiments taken in conjunction with the accompanying drawings.

BRIEF DESCRIPTION OF THE DRAWINGS

FIG. 4 is a view of a screen on a CRT showing surgical procedure selection;

FIG. 10 is a view showing a screen on a CRT showing the detailed data about a surgical instrument;

DESCRIPTION OF THE PREFERRED EMBODIMENTS

One embodiment of the surgical instrument file system in accordance with the present invention will be described with reference to the drawings. Explanation is given as to the case where the above-mentioned binary symbol data code of U.S. Pat. No. 4,939,534 is used for surgical instruments.

Forceps, which is one example of a type of surgical instruments (not shown), includes kocher forceps, pean forceps, mosquito forceps, kelly forceps, right angle forceps, and peritoneum forceps. Surgical scissors, another example, include cooper scissors, mayo scissors, and metzenbaum scissors. A unique data code is attached to each type of these articles. If it is desirable to control the surgical instruments more precisely, a unique data code is attached to an individual article. In this case, the data inherent in each hospital such as receiving date and price are added in addition to the name.

The surface of surgical instrument may be damaged in use or in cleaning. The above-mentioned binary symbol data code of U.S. Pat. No. 4,939,534 is characterized by having large amounts of information in spite of its very small size. Therefore, it is thought that reading may become impossible if the data code is damaged. In the case where the reading by reader becomes impossible, when there is no other means by which to identify the surgical instrument, the surgical instrument must be identified by its shape, which is very inconvenient.

Therefore, to provide against such a case, a unique visually readable code mark is also attached to each surgical instrument. Thus, the surgical instrument can conveniently be identified by comparing the code with the list. This visually readable code mark may be a combination of several numerals and letters or may be a specific article name. As a preventive measure it may be effective to attach the identical optically readable code marks at a plurality of places on one surgical instrument.

Figure 1:
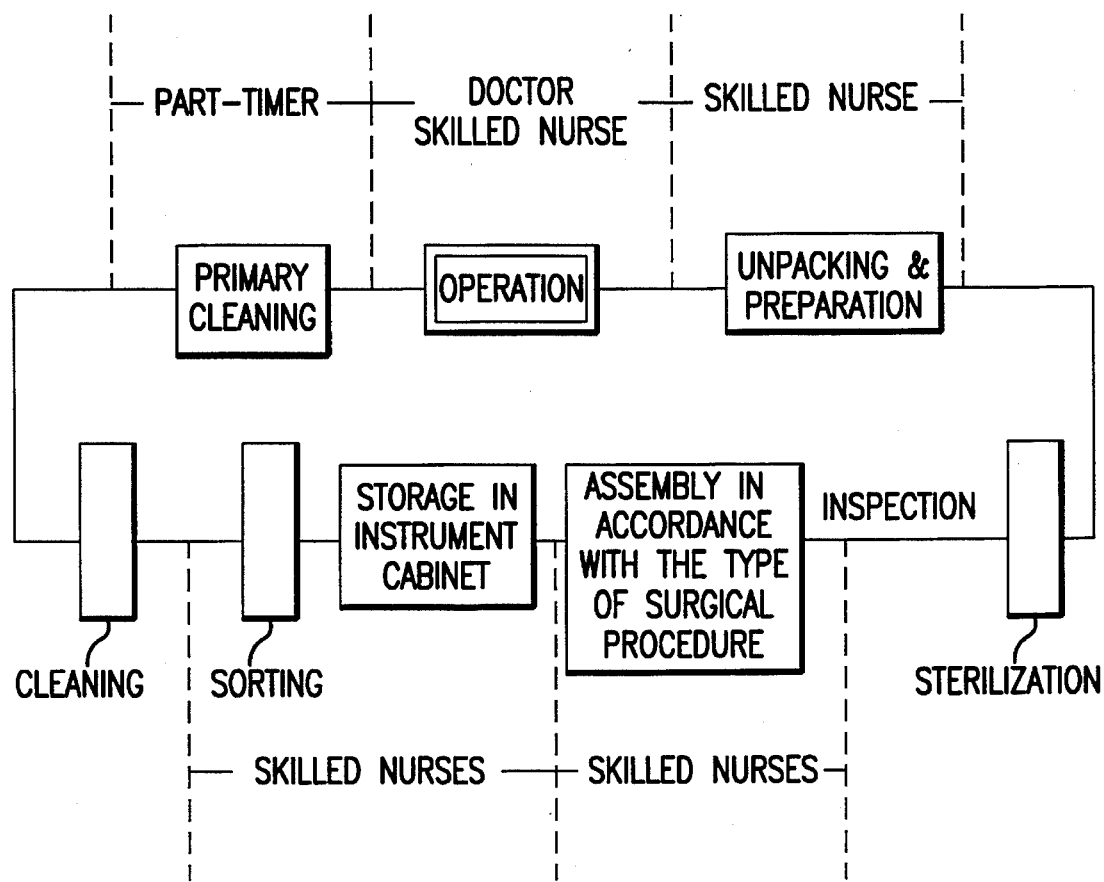
FIG. 1 is a flowchart showing the movement of a surgical instrument in a hospital.
Figure 2:
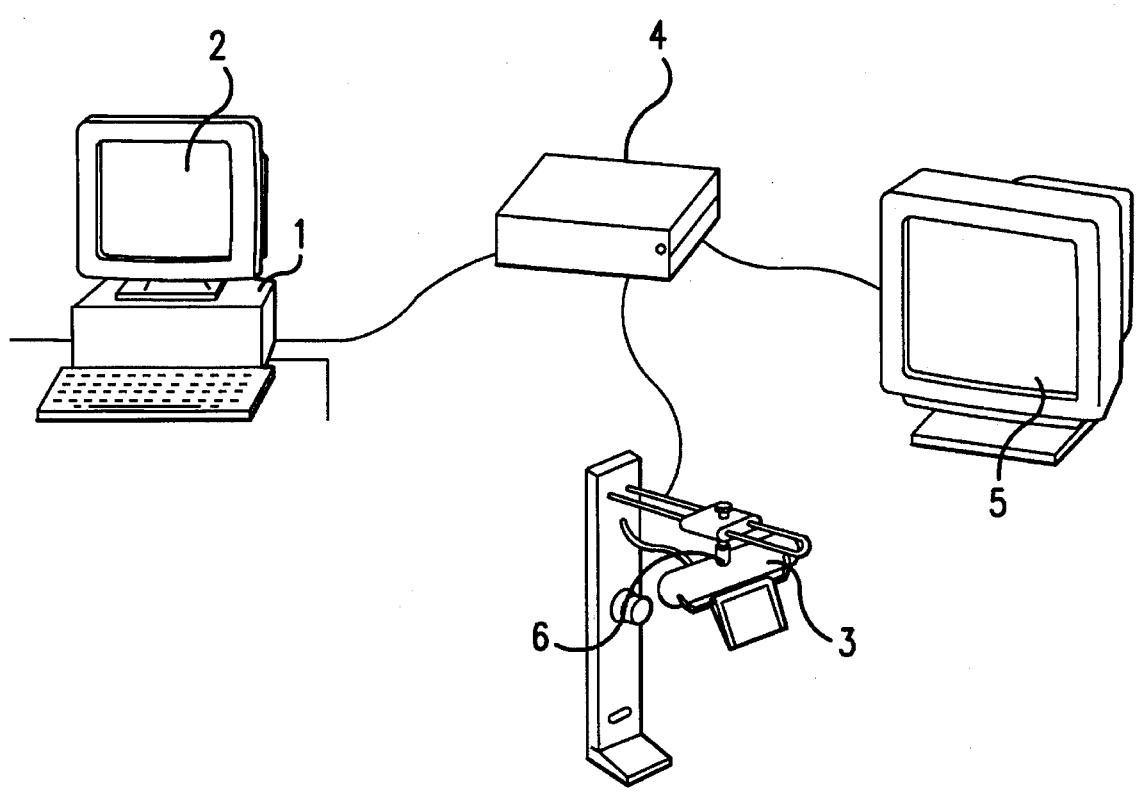
FIG. 2 is a schematic view showing the configuration of the surgical instrument file system in accordance with the present invention.

Next, the system configuration will be described with reference to FIG. 2. Reference numeral (1) denotes a computer, and (2) denotes a CRT screen on which pictures are displayed by as output from the computer. The computer (1) stores the list of surgical instruments required in accordance with the surgical procedure by their names and figures. It also can store the other data for managing the surgical instruments as necessary.

Reference numeral (3) denotes a reader for reading the optically readable code marks which are attached to the surgical instruments, and (4) denotes a controller for converting the above mentioned data code attached as the optically readable code mark into character information. Reference numeral (5) denotes a monitor for checking the position of the data codes read by the reader (3). An operator adjusts the position of the reading portion (6) of the reader (3) while observing the monitor (5) so that the data codes are displayed clearly on the monitor (5).

Next, the procedure for assembling a surgical instrument set by using the above-described surgical instrument file system will be described. First, the computer (1) is used to display the picture shown in FIG. 3 on the CRT screen (2). In the example shown in the figure, an inventory management program for surgical instruments, an educatinal program for learning the name, etc. of surgical instruments, a statistical program for recording the number of operations for each surgical procedure as well as the surgical procedure control program which is an object of the present invention can be selected.

Figure 3:
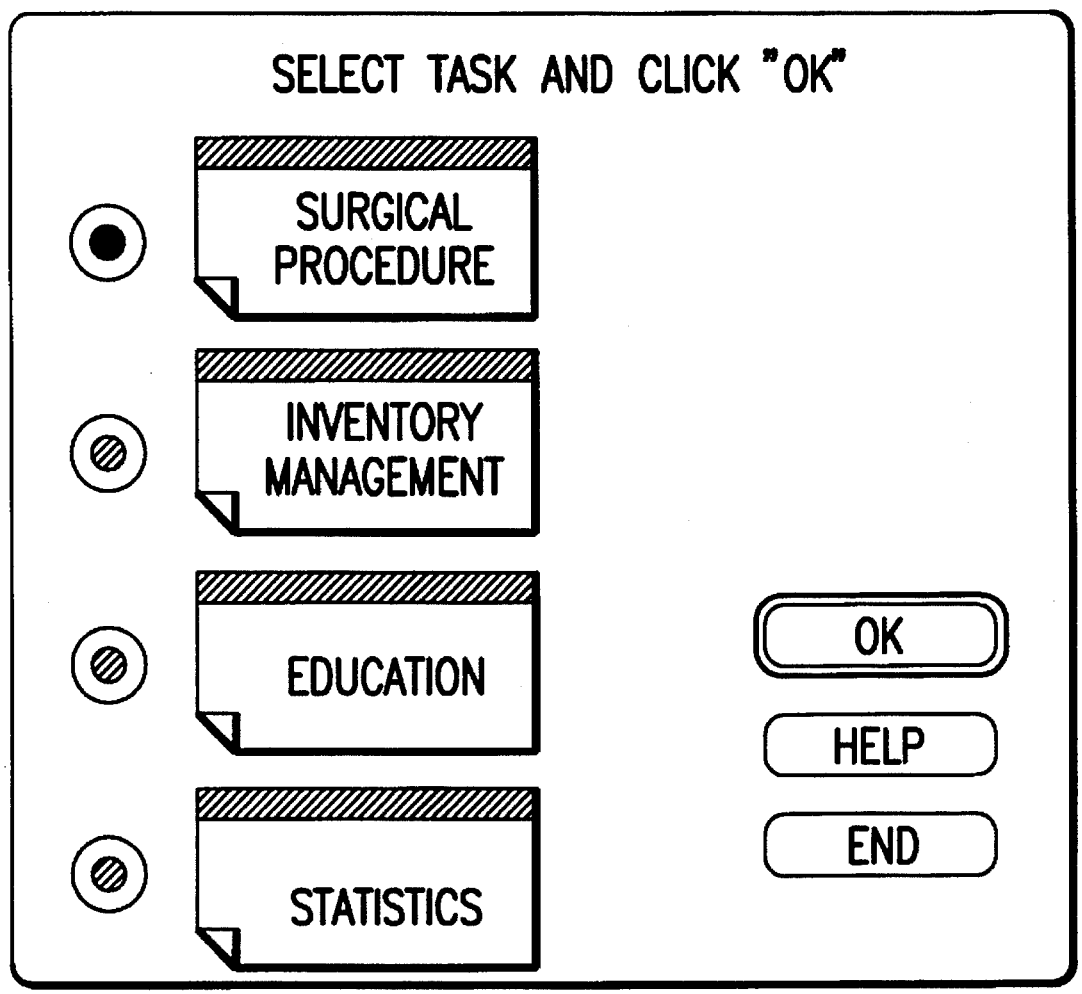
FIG. 3 is a view of a screen on a CRT showing task selection.

When "surgical procedure control" is selected on the picture shown in FIG. 3, the picture shown in FIG. 4 is displayed on the CRT screen (2). On the picture shown in FIG. 4, the department to which the surgical procedure belongs is selected. When the picture of FIG. 4 is first displayed, the name of operation to be performed will not appear. If, for example, "internal medicine" is selected, the list of names of operations performed in the selected "internal medicine" department is displayed.

Figure 5:
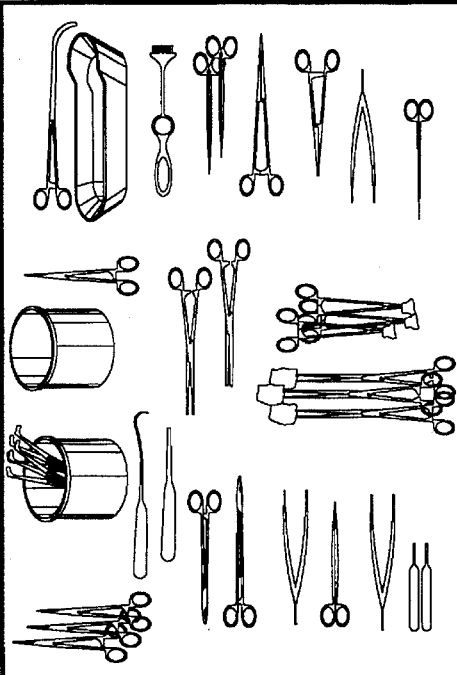
FIG. 5 is a view of a screen on a CRT showing an entire picture for a surgical procedure.
Figure 12:
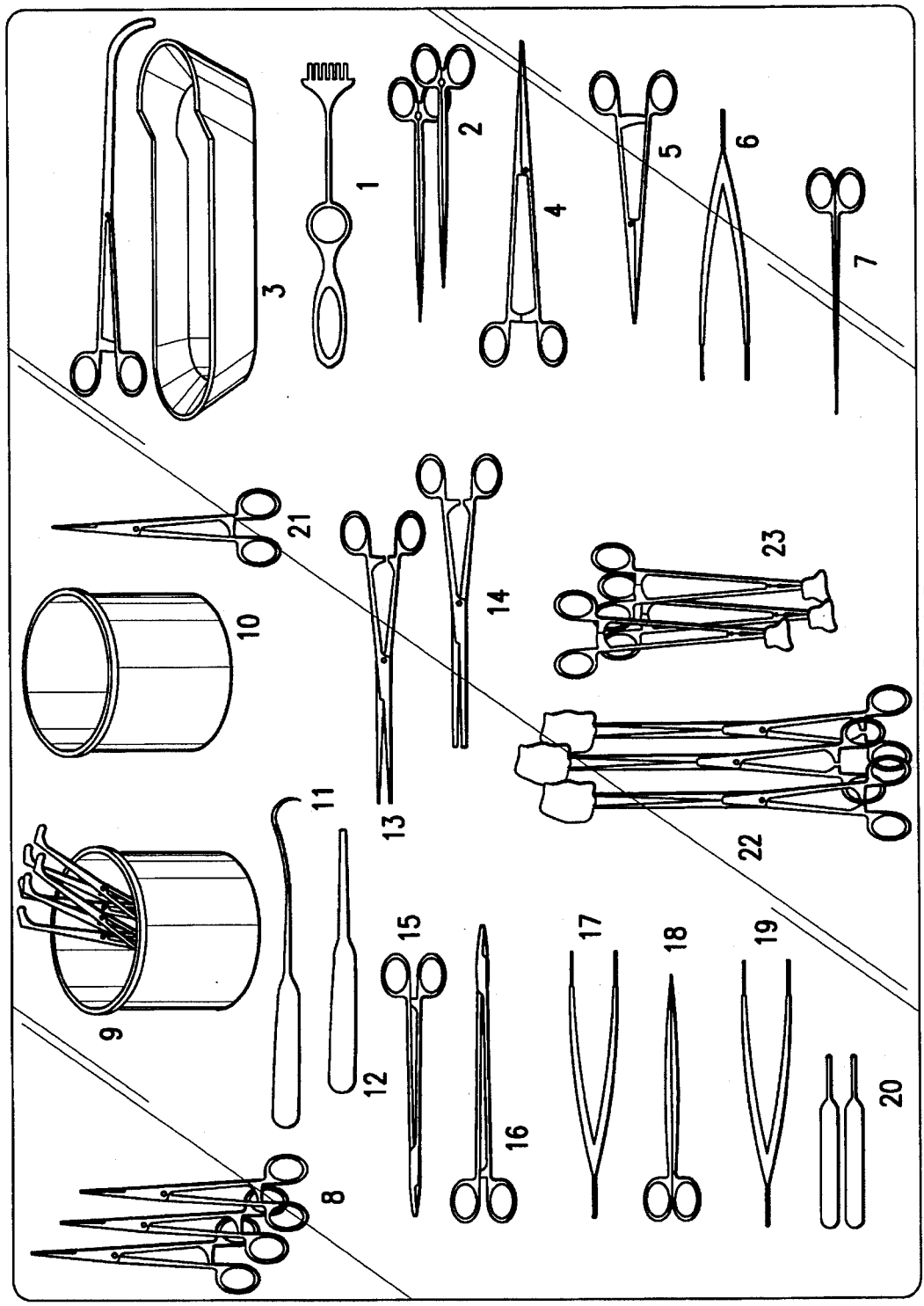
FIG. 12 is a view showing an example of the entire photograph of a surgical instrument set screen for a surgical procedure as shown in FIG. 5.

If, for example, "gastroduodenum" is selected, the entire picture of the surgical operation shown in FIG. 5 is displayed on the CRT screen (2). On the screen shown in FIG. 5, the photograph of all surgical instruments in a set as shown in FIG. 12 is displayed. In addition, a list of single articles, a method of sterilization for the surgical instruments, the size of container needed for the surgical instruments, etc. is also displayed for greater convenience for the workers.

Figure 13:
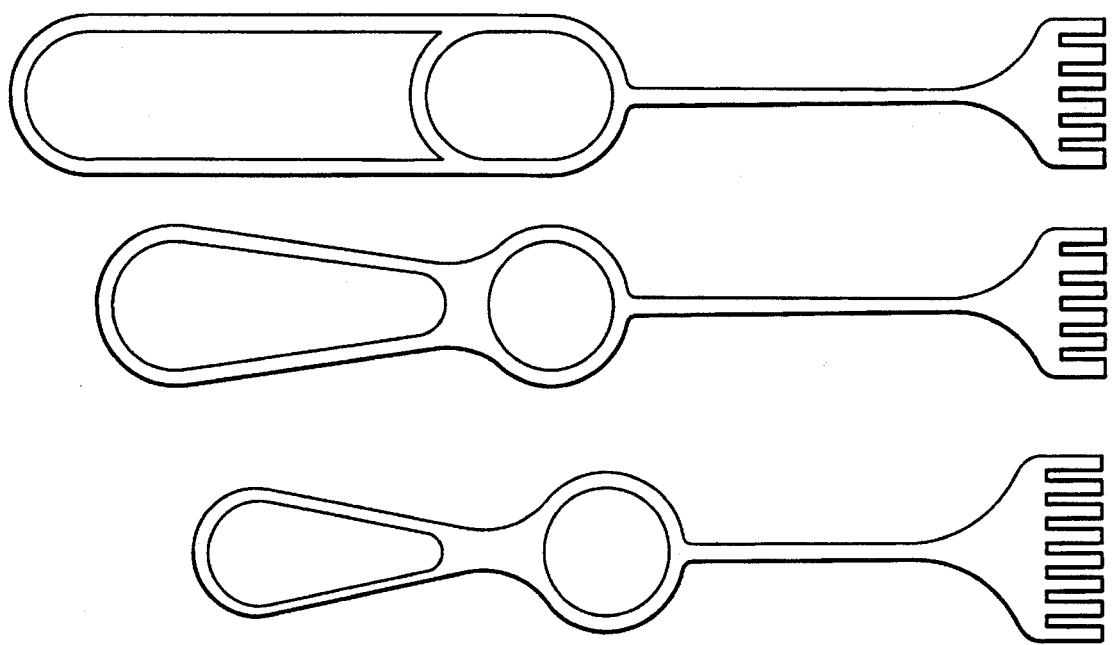
FIG. 13 is a view showing an example of the portion corresponding to Photo 1 on the screen shown in FIG. 10 showing the detailed data.
Figure 14:
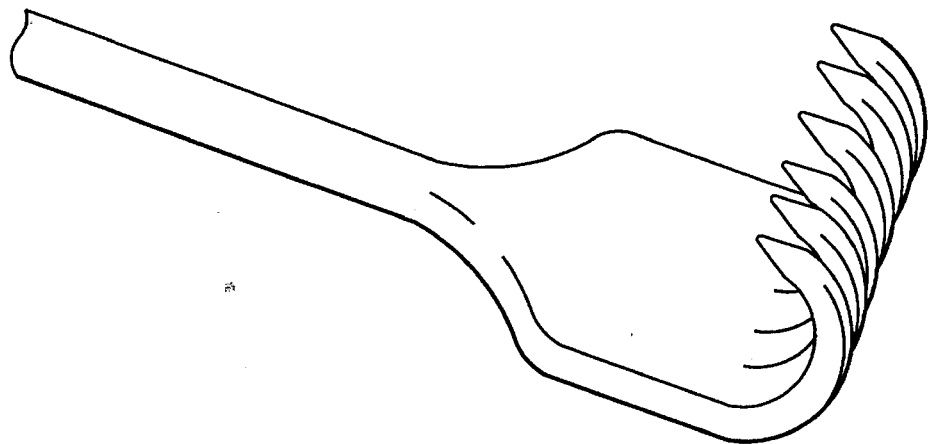
FIG. 14 is a view showing an example of the portion corresponding to Photo 2 on the screen shown in FIG. 10 showing the detailed data.

When the list of single articles is used, when one article is selected by its name, the detailed data for that surgical instrument is displayed, and additionally an expanded photograph of the surgical instrument can be displayed as shown in FIG. 10. If this enlarged photograph is selected, the enlarged pictures of the surgical instrument are successively displayed as shown in FIGS. 13 and 14. By referring to this enlarged photograph, the required surgical instrument can be easily looked for.

Figure 6A:
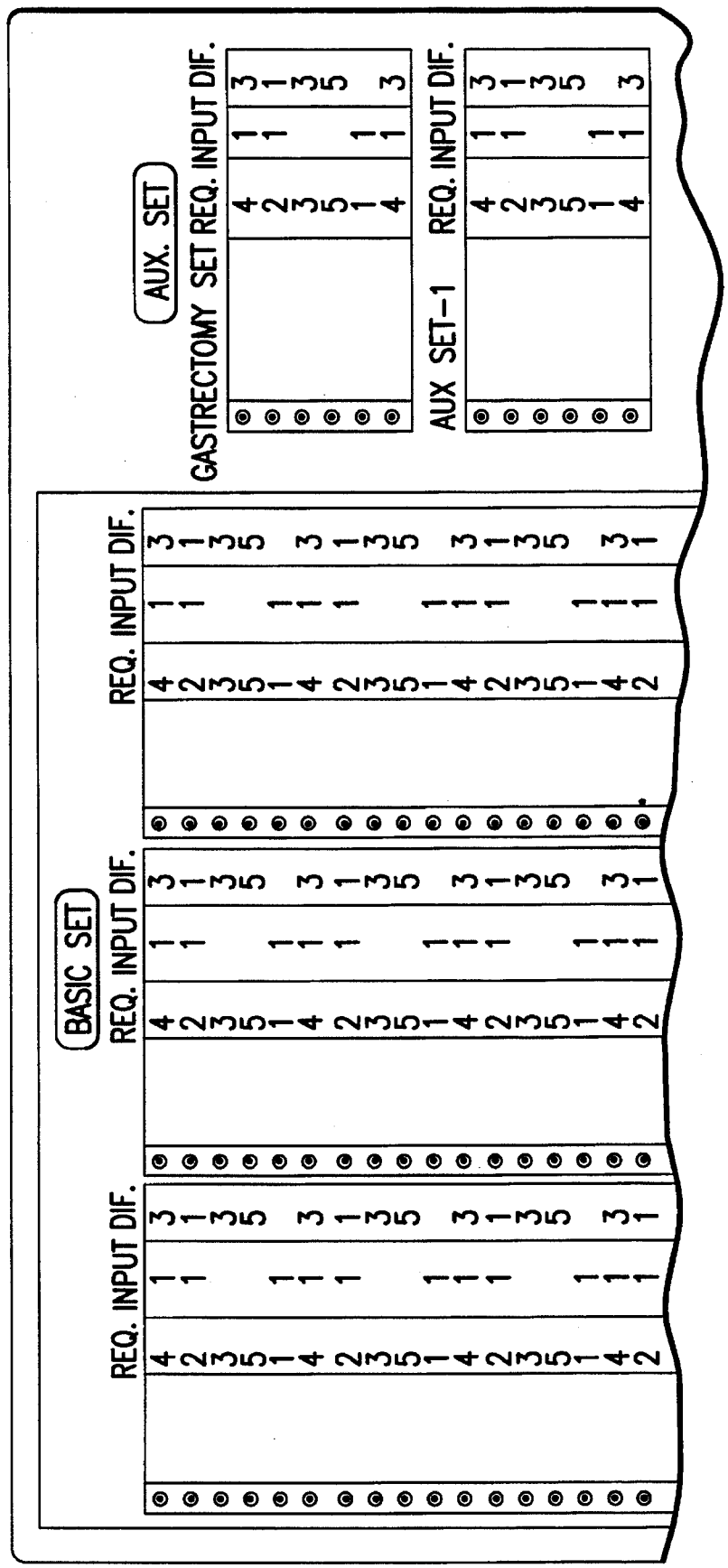
FIG. 6 is a view of a screen on a CRT showing a list.
Figure 6B:
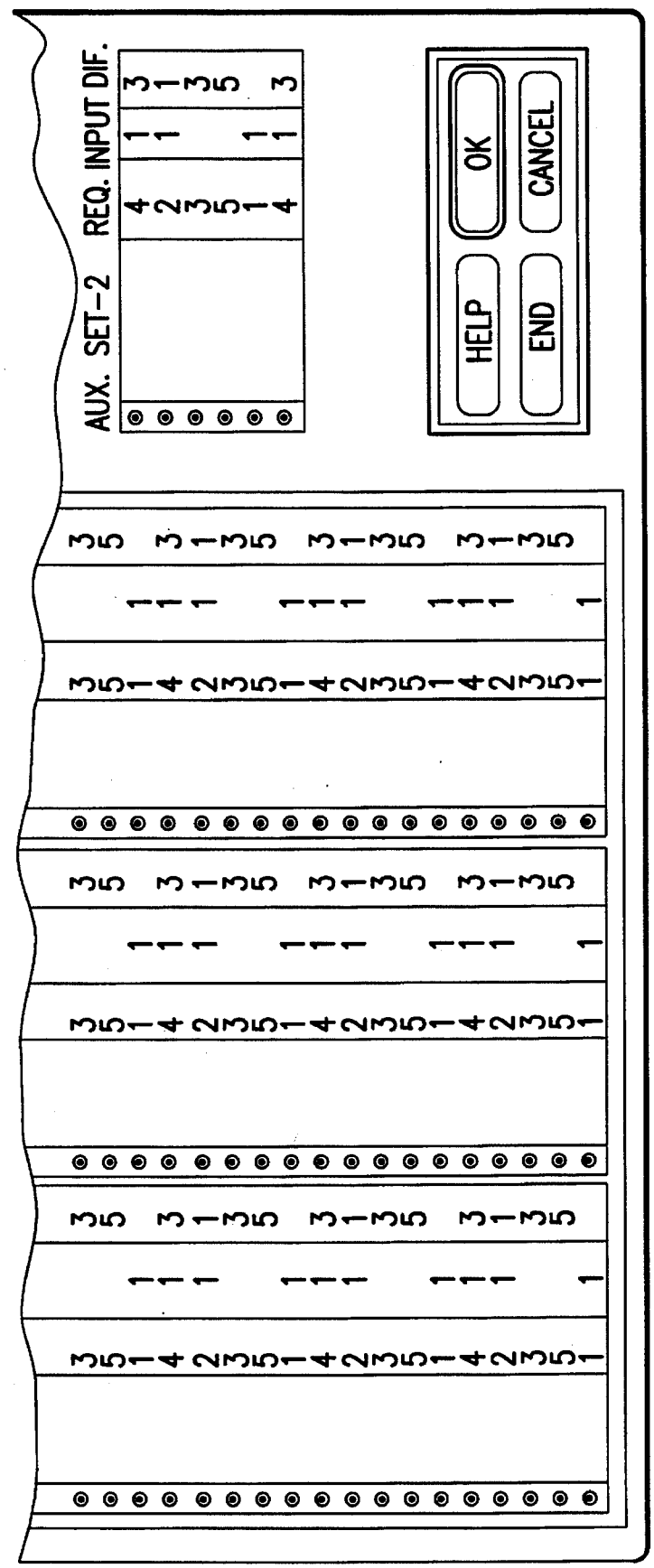

After the picture of the entire surgical instrument set is examined on the screen in FIG. 5, the next screen shown in FIG. 6 is selected. A list of names of surgical instruments used for the selected surgical procedure is displayed on the CRT screen (2). On the CRT screen (2), the names and number of required surgical instruments are displayed in the form of a list.

While the list as displayed, surgical instruments which are thought to be equivalent to the surgical instruments listed on the screen are taken out successively, and the data code on the surgical instrument is read by the reader (3) while being checked by the monitor 5. Thus, the reading and checking are performed.

When the data code, being in focus, is read, the surgical instrument marked with the data code is entered into the computer (1) through the controller (4). In this manner, the data codes of the surgical instruments whose names appear in the list are successively read by the reader (3) and inputted into the computer (1). Thus, the number of the appropriate surgical instruments is added successively. When it has been confirmed that there is a multiple number of identical surgical instruments, the direct checking can be performed manually. The required number, the inputted number, and the difference between the two for each surgical instrument is displayed so that the state of the assembled set can be seen at a glance.

Figure 7:
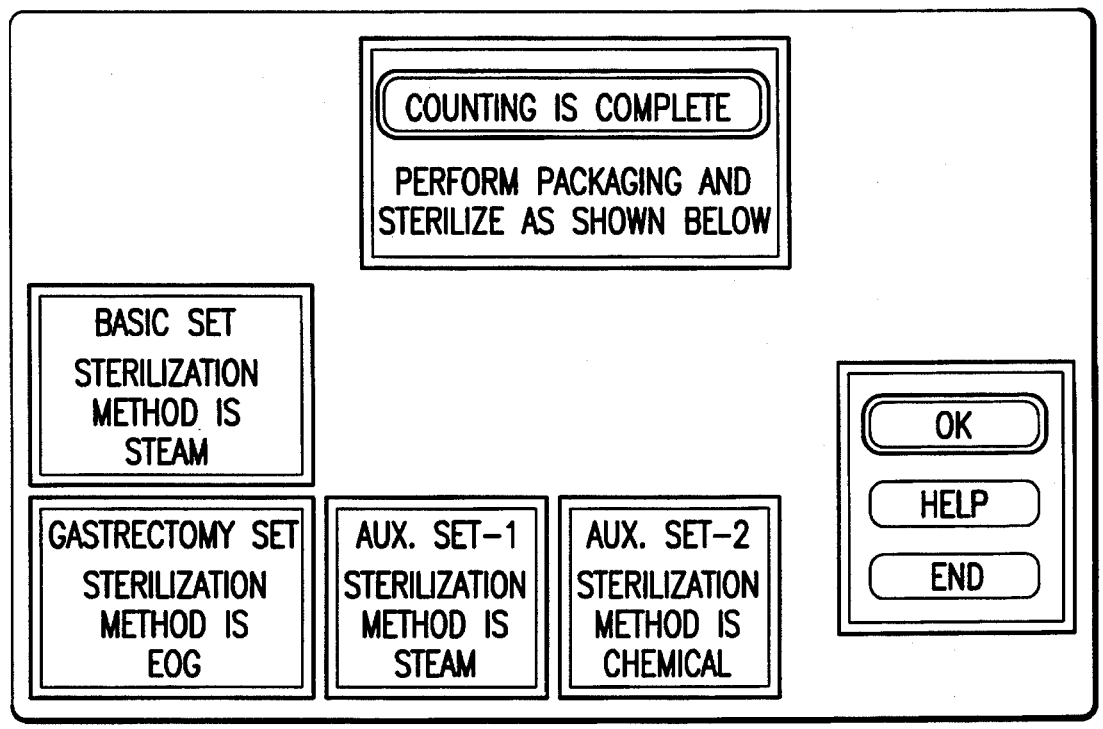
FIG. 7 is a view of a screen on a CRT showing set completion.
Figure 8:
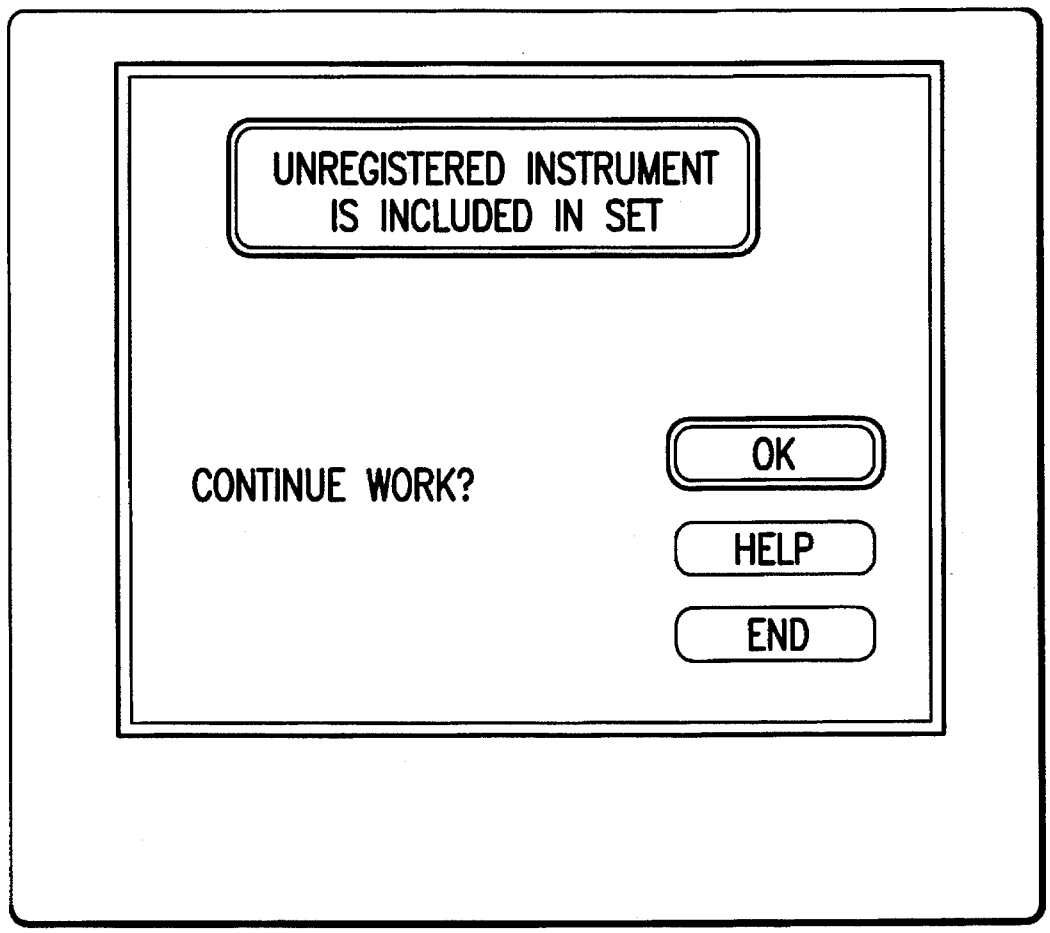
FIG. 8 is a view of a screen on a CRT showing the inclusion of an unregistered instrument.
Figure 9:
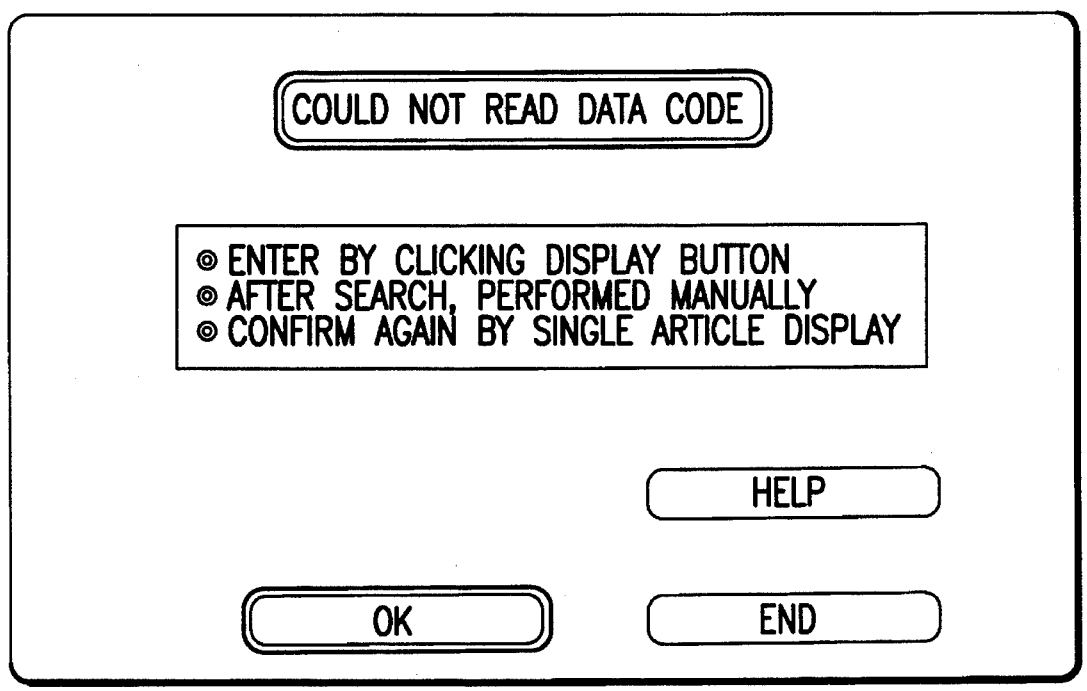
FIG. 9 is a view of a screen on a CRT showing an entry error.

The assembly of each set unit (i.e. basic set and an auxiliary set) is performed. When the counting is completed, the screen shown in FIG. 7 is displayed, so that the completion of each set component such as the basic set and the surgical set for gastrectomy can be confirmed. If an instrument whose name is not contained in the list is read, the screen shown in FIG. 8 is displayed, alerting the operator that an instrument which is not registered in the set is included.

Figure 11:
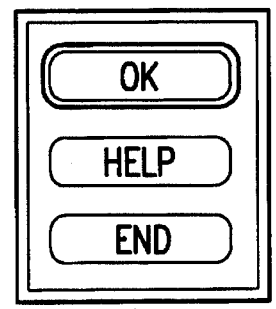
FIG. 11 is a view of a screen on a CRT showing set completion.

When the checking of all sets is completed, the screen shown in FIG. 11 is displayed, showing that the set assembly process has been completed. Also, the sterilization method in accordance with the surgical procedure is displayed together with the set completion message. Therefore, if sterilization is performed by following the instructions, the preparation of surgical instruments for the surgical procedure is completed.

In the case where the surgical instrument corresponding to a name is unknown when the list shown in FIG. 6 is displayed, the entire picture of the surgical instrument as shown in FIG. 5 can be displayed. Each surgical instrument carries a number corresponding to the number on single article list as shown in FIG. 12, so that the proper surgical instrument can be searched for by looking at the screen shown in FIG. 12. If this entire picture is too small to identify the surgical instrument, an enlarged photograph of the individual surgical instrument as shown in FIGS. 13 and 14 is displayed in position Photo 1 or Photo 2 in FIG. 10. By referring to this enlarged photograph, the required surgical instrument can be easily searched for.

When an unskilled person who is unfamiliar with the names of surgical instruments assembles a surgical instrument set, it may be possible to assemble the surgical instruments by using the screen shown in FIG. 5 and by referring to the screen in FIG. 10 as necessary, without using the list shown in FIG. 6.

In this case, a surgical instrument which is thought to be equivalent to the indicated surgical instrument is taken out while looking at the picture on the screen. Then, the data code on the surgical instrument is read by the reader (3) and inputted into the computer (1). The number of read instruments is recorded in the single article list so that the set assembly state becomes known, or the surgical instrument read in the entire picture is identified, so that the set assembly state is apparent.

Next, the effect of the present invention will be described.

As described above, the surgical instrument file system in accordance with the present invention is comprised of a screen on which the names and pictures of the surgical instruments required for a surgical procedure are selectively displayed; surgical instruments to which a unique optically readable code mark is attached; a reader for reading the optically readable code mark; and a computer which stores the data about the surgical instruments required for the surgical procedure and into which the information from the optically readable code mark is inputted. The reader reads the optically readable code mark on surgical instrument and the information contained in the optically readable code mark is inputted into the computer, after which the inputted surgical instruments are successively identified on the screen, and finally the preparation of surgical instrument set can be confirmed. Therefore, anyone, not limited to skilled nurses, can put together surgical instrument sets, which will alleviate the recent shortage of nurses. Also, since the surgical instruments can be identified using a picture, the surgical instruments can be assembled correctly even if the formal name of an individual instrument is unknown. Therefore, the level of safety of medical treatment can be improved.

If a unique visually readable code mark is attached to the surgical instrument in addition to the unique optically readable code mark, a surgical instrument can be identified immediately even when the reading of the optically readable code mark becomes impossible due to damage or the like. Therefore, the surgical instrument sets can be still assembled correctly.

Figure 15:
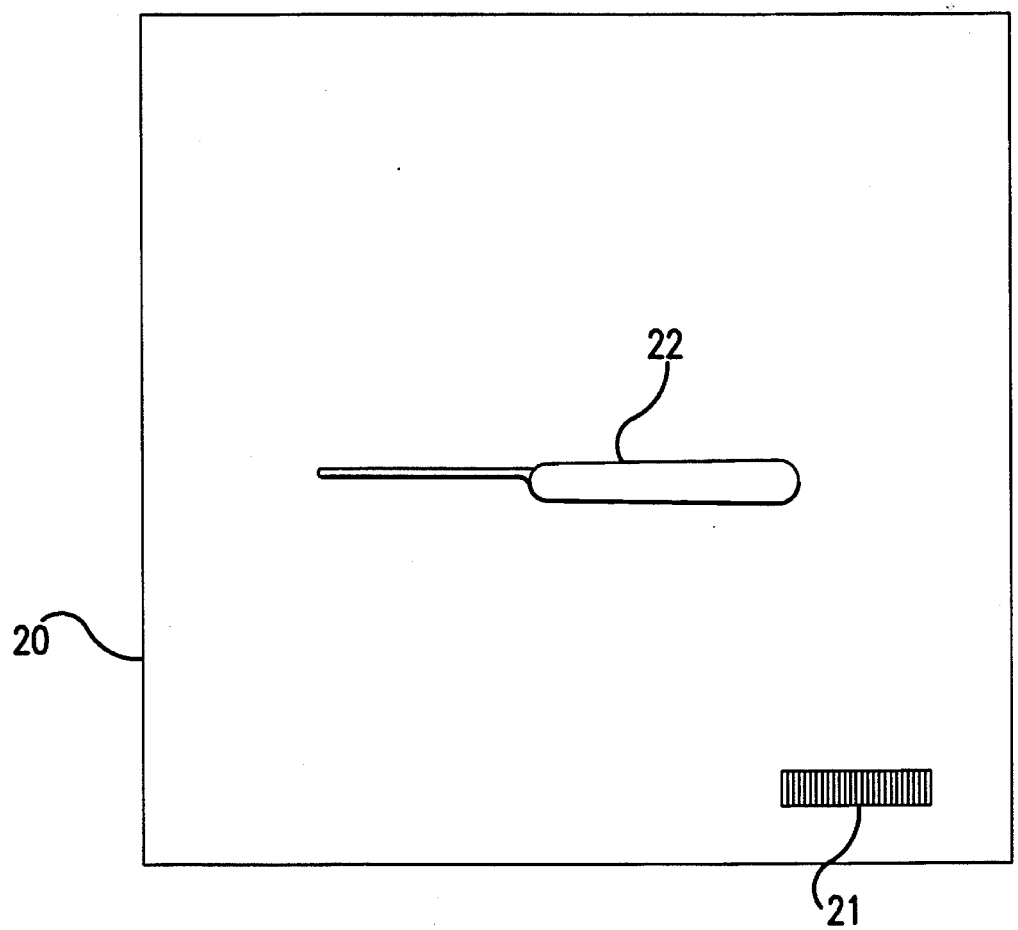
FIG. 15 is a view showing a pictorial representation of a surgical instrument in which the pictorial representation has an optically readable code mark.
Figure 16:
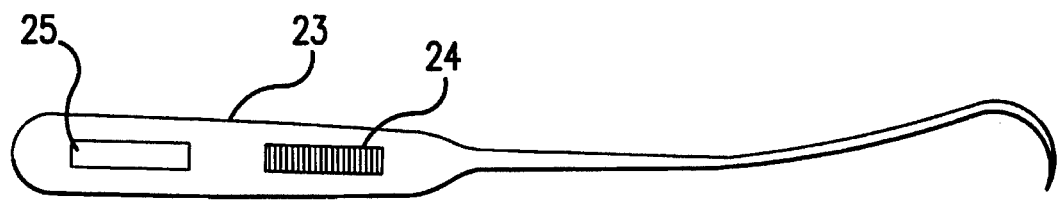
FIG. 16 is a view showing a surgical instrument which has an optically readable code mark and a visually readable code mark.

FIG. 15 shows a pictorial representation, for example, a photograph 20 of a surgical instrument 22, the photograph 20 having an optically readable code mark 21. FIG. 16 shows a surgical instrument 23 having an optically readable code mark 24 and a visually readable code mark 25.

Although the invention has been described in specific terms, it is to be understood that the described embodiment is only illustrative and various changes and modifications may be imparted thereto without departing from the scope of the invention which is limited solely by the appended claims.

What is claimed is:

1. A surgical instrument assembly system for enhancing the safety of surgical procedures and which can be used by minimally skilled medical personnel for selecting and assembling surgical instruments to be sterilized and to be used for surgical procedures after being sterilized comprising:

a plurality of surgical instruments each having a readable code;

a reader for reading said codes on the surgical instruments presented to said reader;

a computer for storing data relating to the surgical instruments required for various surgical procedures;

said reader having means operable to input into said computer data relating to the codes read by said reader of the surgical instruments presented to said reader;

first selection means on said computer for selecting a surgical procedure such that said computer displays a list of the names of all of the surgical instruments required for said selected procedure;

second selection means on said computer for selecting the display of a pictorial representative of said surgical instruments on said list;

first indicating means on said computer indicating that the codes of all of the surgical instruments on said list have been read by said reader and inputted into said computer to thereby confirm that the surgical instruments required for the selected procedure have been presented to the reader; and second indicating means on said computer indicating the type of Sterilization required for the surgical articles on said list;

whereby the safety of the surgical procedure is enhanced in that confirmation that the correct surgical instruments required for the selected surgical procedure has been selected and assembled although the selection and assembly was made by minimally skilled medical personnel.

2. A surgical instrument assembly system according to claim 1 wherein said indicating means is designated a first indicating means, and further comprising a second indicating means indicating that said reader has read the code of an instrument not included on said list of surgical instruments for said selected procedure.

3. A surgical instrument assembly system according to claim 1 wherein said computer has display means operable to display said list of the names of all of the surgical instruments required for said selected procedure, to display the names of those surgical instruments having codes which have been presented to said reader and which have been read by said reader and inputted to said computer, and to display the names of those surgical instruments which are included on said list but which have not been presented to said reader, whereby the status of the assembly of said surgical instruments required for said selected procedure can be viewed at a glance on said display means.

4. A surgical instrument assembly system according to claim 1 wherein said computer has display means operable to simultaneously display a pictorial representation of a plurality of surgical instruments included on said list, said second selection means being operable to selectively display on said display means a selected one of said plurality of surgical instruments on a larger scale than the scale on which said plurality of surgical instruments were simultaneously displayed.

5. A surgical instrument assembly system according to claim 1 further comprising a monitor connected to said reader and operable to display the codes read by said reader.

6. A method of assembling surgical instruments to be sterilized and to be used for a surgical procedure, the method enhancing the safety of the surgical procedure and being usable by minimally skilled medical personnel comprising:

affixing a readable code to each of said surgical instruments;

utilizing a reader to read said codes and to input data relating to said surgical instruments to a computer having a display;

selecting on said computer a surgical procedure of which a predetermined plurality of surgical instruments are to be used;

displaying on said display a list of the names of said plurality of surgical instruments to be used in said selected procedure;

displaying a pictorial representation of said surgical instruments to be used in said selected procedure;

utilizing said computer to provide an indication that the codes of all of the surgical instruments on said list have been read by said reader and inputted to said computer to thereby confirm that the surgical instruments required for said selected procedure have all been assembled and utilizing said computer to provide an indication of the type of sterilization required for sterilizing the surgical instruments on said list:

whereby the safety of the surgical procedure is enchanced in that confirmation that the correct surgical instruments required for the selected surgical procedure has been selected although the selection was made by minimally skilled medical personnel.

7. A method of assembling surgical instruments for a surgical procedure according to claim 6 further comprising the steps of simultaneously with said step of displaying on said display said list of the names of said plurality of surgical instruments to be used with said selected procedure also displaying the names of those surgical instruments which have been presented to said reader and which have been read by said reader and inputted to said computer and also displaying the names of those surgical instruments which are included on said list but which have not been presented to the reader, whereby the status of the assembly of the required instruments for said selected procedure can be viewed at a glance.

8. A method of assembling surgical instruments for a surgical procedure according to claim 6 further comprising indicating that the reader has read the code of a surgical instrument not included on said list of surgical instruments for said selected procedure.

9. A method of assembling surgical instruments for a surgical procedure according to claim 8 wherein said step of displaying a pictorial representation of said surgical instruments further comprises selectively displaying a selected one of said simultaneously displayed instruments on a larger scale than the scale on which said plurality of surgical instruments were simultaneously displayed.

10. A method of assembling surgical instruments for a surgical procedure according to claim 6 wherein said step of displaying a pictorial representation of said surgical instruments comprises simultaneously displaying a pictorial representation of a plurality of said surgical instruments on said display.

11. A method of assembling surgical instruments for a surgical procedure according to claim 6 further comprising displaying on a monitor the codes read by said reader.

12. A surgical instrument assembly system for enhancing the safety of surgical procedure and which can be used by minimally skilled personnel for assembling surgical instruments to be sterilized and to be used for surgical procedures after being sterilized comprising:

a plurality of surgical instruments each having a readable code;

a reader for reading said codes on the surgical instruments presented to said reader;

a computer for storing data relating to the surgical instruments required for various surgical procedures;

said reader having means operable to input into said computer data relating to the codes read by said reader of the surgical instruments presented to said reader;

first selection means on said computer for selecting a surgical procedure such that said computer displays a list of the names of all of the surgical instruments required for said selected procedure;

second selection means on said computer for selecting the display of a pictorial representative of said surgical instruments on said list;

first indicating means on said computer indicating that the codes of all of the surgical instruments on said list have been read by said reader and inputted into said computer to thereby confirm that the surgical instruments required for the selected procedure have been presented to the reader;

second indicating means on said computer indicating the type of sterilization required for sterilizing the surgical instrument on said list:

said list of the names of the surgical instruments for a selected procedure including at least one surgical instrument which does not carry said code; and a pictorial representative of said at least one surgical instrument, said pictorial representation having a code which is readable by said reader and inputted to said computer;

whereby the safety of the surgical procedure is enhanced in that confirmation that the correct surgical instruments required for the selected surgical procedure has been selected although the selection was made by minimally skilled medical personnel.

13. A surgical instrument assembly system according to claim 12 wherein said pictorial representation is a photograph.

14. A surgical instrument assembly system according to claim 12 where said at least one surgical instrument is too small to carry such code.

15. A method of assembling surgical instruments to be sterilized and to be used for a surgical procedure, the method enhancing the safety of the surgical procedure and being usable by minimally skilled medical personnel comprising:

affixing a readable code to each of said surgical instruments;

utilizing a reader to read said codes and to input data relating to said surgical instruments to a computer having a display;

selecting on said computer a surgical procedure of which a predetermined plurality of surgical instruments are to be used;

displaying on said display a list of the names of said plurality of surgical instruments to be used in said selected procedure;

displaying a pictorial representation of said surgical instruments to be used in said selected procedure;

utilizing said computer to provide an indication that the codes of all of the surgical instruments on said list have been read by said reader and inputted to said computer to thereby confirm that the surgical instruments required for said selected procedure have all been assembled;

utilizing said computer to provide an indication of the type of sterilization required for sterilizing instruments on said list:

at least one of said surgical instruments included in said list does not have an affixed code, providing a pictorial representation of said one surgical instrument;

affixing said code to said pictorial representation;

presenting said pictorial representation to said reader;

reading said code on said pictorial representation; and inputting data relating to said one surgical instrument to said computer;

whereby the safety of the surgical procedure is enhanced in that confirmation that the correct surgical instruments required for the selected surgical procedure has been selected although the selection was made by minimally skilled medical personnel.

16. A method of assembling surgical instruments for a surgical procedure according to claim 15 wherein said pictorial representation is a photograph of the surgical instrument.

17. A surgical article assembly system for enhancing the safety of surgical procedures and which can be used by minimally skilled medical personnel for assembling surgical articles to be sterilized and to be used for surgical procedures after sterilization comprising:

a first plurality of surgical articles each having a readable code;

at least one other surgical article;

a pictorial representation of each of said other surgical articles;

a readable code on each of said pictorial representations;

a reader for reading said codes on said first plurality of surgical articles and for reading said codes on said pictorial representations;

a computer for storing data relating to the surgical articles required for various surgical procedures;

said reader having means operable to input into said computer data relating to the codes read by said reader of said first plurality of surgical articles presented to said reader and data relating to the codes read by the reader of the pictorial representations presented to the reader;

first selection means on said computer for selecting a surgical procedure such that said computer displays a list of the names of all of the surgical articles required for the selected surgical procedure;

first indicating means on said computer indicating that the codes of all of said first plurality of surgical articles on said list and all of the codes of said pictorial representations of all of said other surgical articles on said list have been read by said reader and inputted into said computer to thereby confirm that the surgical articles of said first plurality of surgical articles and the pictorial representations of said other surgical articles required for the selected procedure have been presented to the reader;

second indicating means on said computer indicating the type of sterilization required for the surgical articles on said list:

whereby the safety of the surgical procedure is enhanced in that confirmation that the correct surgical articles required for the selected surgical procedure has been selected although the selection was made by minimally skilled medical personnel.

18. A surgical article assembly system according to claim 17 wherein said pictorial representation is a photograph.

19. A surgical article assembly system according to claim 17 wherein said pictorial representation is a drawing.

20. A surgical article assembly system according to claim 17 wherein said surgical article comprise linens.

21. A surgical article assembly system according to claim 17 wherein said surgical article comprises medicines.

22. A surgical article assembly system according to claim 17 wherein said surgical article comprises disposable supplies.

23. A surgical instrument assembly system for enhancing the safety of surgical procedures and which can be used by minimally skilled medical personnel for assembling surgical articles to be sterilized and to be used for surgical procedures after sterilization comprising:

a plurality of surgical articles each having a readable code;

an illustration of each of said surgical articles;

a readable code on each of said illustrations;

a reader for reading said codes on the illustrations presented to said reader;

a computer for storing data relating to the surgical articles required for various surgical procedures;

said reader having means operable to input into said computer data relating to the codes read by said reader of the illustrations of the surgical articles presented to said reader;

first selection means on said computer for selecting a surgical procedure such that said computer displays a list of the names of all of the surgical articles required for said selected procedure;

second selection means on said computer for selecting a pictorial display of said surgical articles on said list;

first indicating means on said computer indicating that the codes of the illustrations of all of the surgical articles on said list have been read by said reader and inputted into said computer to thereby confirm that the illustrations of the surgical articles required for the selected procedure have been presented to the reader; and second indicating means on said computer indicating the type of sterilization required for the surgical articles on said list:

whereby the safety of the surgical procedure is enhanced in that confirmation that the correct surgical articles instruments required for the selected surgical procedure has been selected although the selection was made by minimally skilled medical personnel.

24. A surgical article assembly system for enhancing the safety of surgical procedures and which can be used by minimally skilled medical personnel for assembling surgical articles to be sterilized and to be used for surgical procedures after sterilizing comprising:

a first plurality of surgical articles each having a readable code;

at least one other surgical article having an identifying readable code representing the respective at least one other surgical article;

a pictorial representation of each of said at least one other surgical article;

an identifying readable code on each of said pictorial representations with each identifying readable code on said pictorial representation representing the respective at least one other surgical article such that the identifying readable code on said pictorial representation of said at least one other surgical article is the same as the identifying readable code on said respective at least one other surgical article;

a reader for reading said readable codes on said first plurality of surgical articles, for reading said identifying readable codes on said at least one surgical article and for reading said identifying readable codes on said pictorial representations;

a computer for storing data relating to the surgical articles required for various surgical procedures;

said reader having means operable to input into said computer data relating to the readable codes read by said reader of said first plurality of surgical articles presented to said reader, data relating to the identifying readable codes read by said reader of said at least one surgical article presented to the reader and data relating to the identifying readable codes read by the reader of said pictorial representations presented to the reader;

first selection means on said computer for selecting a surgical procedure such that said computer displays a list of the names of all of the surgical articles required for the selected surgical procedure;

first indicating means on said computer indicating that the readable codes of all of said first plurality of surgical articles on said list have been read by said reader and inputted to said computer and that the identifying codes representing all of said at least one other surgical article on said list have been read by said reader and inputted to said computer to thereby confirm that the surgical articles of said first plurality of surgical articles and said at least one other surgical article required for said selected procedure have been presented to the reader; and second indicating means on said computer indicating the type of sterilization required for the surgical articles on said list;

whereby the safety of the surgical procedure is enhanced in that confirmation that the correct surgical articles instruments required for the selected surgical procedure has been selected although the selection was made by minimally skilled medical personnel.

25. A surgical article assembly system according to claim 24 wherein said at least one other surgical article includes a surgical item, said identifying readable code on said surgical item being the same as the identifying readable code on the pictorial representation of said surgical item, said at least one other surgical article being presented to said reader by a surgical article assembler, said surgical article assembler selectively presenting to said reader either said identifying readable code on said identifying item or the identifying readable code on the pictorial representation of said identifying item.

* * * * *